United States Patent
Gödiker et al.

(10) Patent No.: US 11,547,638 B2
(45) Date of Patent: Jan. 10, 2023

(54) LOW-MELTING GLASS CERAMIC

(71) Applicant: Vita Zahnfabrik H. Rauter GmbH & Co. KG, Bad Säckingen (DE)

(72) Inventors: Berit Gödiker, Bad Säckingen (DE); Michael Hackner, Lörrach (DE)

(73) Assignee: Vita Zahnfabrik H. Rauter GmbH & Co. KG, Bad Säckingen (DE)

( * ) Notice: Subject to any disclaimer, the term of this patent is extended or adjusted under 35 U.S.C. 154(b) by 323 days.

(21) Appl. No.: 16/858,865

(22) Filed: Apr. 27, 2020

(65) Prior Publication Data

US 2020/0345589 A1 Nov. 5, 2020

(30) Foreign Application Priority Data

May 3, 2019 (EP) ................................ 19172510
Apr. 21, 2020 (EP) ................................ 20170631

(51) Int. Cl.
| | |
|---|---|
| C03C 10/10 | (2006.01) |
| C03B 32/02 | (2006.01) |
| A61K 6/802 | (2020.01) |
| C03C 8/02 | (2006.01) |
| C03C 10/00 | (2006.01) |

(52) U.S. Cl.
CPC ............. *A61K 6/802* (2020.01); *C03B 32/02* (2013.01); *C03C 8/02* (2013.01); *C03C 10/0027* (2013.01); *C03C 10/0054* (2013.01); *C03C 2204/00* (2013.01); *C03C 2205/06* (2013.01)

(58) Field of Classification Search
CPC ....... C03C 10/0018; A61K 6/827; A61K 6/833
See application file for complete search history.

(56) References Cited

U.S. PATENT DOCUMENTS

| | | | |
|---|---|---|---|
| 6,121,175 A | 9/2000 | Drescher et al. | |
| 6,455,451 B1 | 9/2002 | Brodkin et al. | |
| 6,706,654 B2* | 3/2004 | van der Zel | A61K 6/827 |
| | | | 264/16 |
| 7,183,232 B2 | 2/2007 | van't Hoen et al. | |
| 10,988,403 B2* | 4/2021 | Kawata | C03C 4/0021 |
| 2002/0066233 A1* | 6/2002 | McArdle | C04B 35/00 |
| | | | 51/308 |
| 2002/0198093 A1* | 12/2002 | van der Zel | A61K 6/833 |
| | | | 106/35 |
| 2003/0226475 A1* | 12/2003 | Stern | A61C 13/083 |
| | | | 106/35 |
| 2010/0035215 A1 | 2/2010 | Brodkin et al. | |
| 2011/0021336 A1 | 1/2011 | Bolle et al. | |
| 2013/0149433 A1 | 6/2013 | Ehrt et al. | |
| 2015/0376067 A1* | 12/2015 | Kuntz | A61C 13/082 |
| | | | 433/201.1 |

(Continued)

FOREIGN PATENT DOCUMENTS

| | | |
|---|---|---|
| DE | 10340597 A1 | 3/2005 |
| DE | 10 2010 035 545 A1 | 3/2012 |
| EP | 0 468 435 A2 | 1/1992 |

(Continued)

*Primary Examiner* — Karl E Group
(74) *Attorney, Agent, or Firm* — Dority & Manning, P.A.

(57) ABSTRACT

The present invention relates to a glass ceramic for veneering a dental frame structure, wherein said glass ceramic is characterized by a high content of $B_2O_3$, to a process for the preparation thereof, and to the use thereof in the production of dental restorations.

20 Claims, 1 Drawing Sheet

(56) References Cited

U.S. PATENT DOCUMENTS

2019/0322567 A1* 10/2019 Kawata .................. C03C 3/087

FOREIGN PATENT DOCUMENTS

| EP | 1 514 850 A1 | 3/2005 |
| EP | 3 366 260 A1 | 8/2018 |
| EP | 3 536 301 A1 | 9/2019 |
| NL | 1017895 C2 | 10/2002 |

* cited by examiner

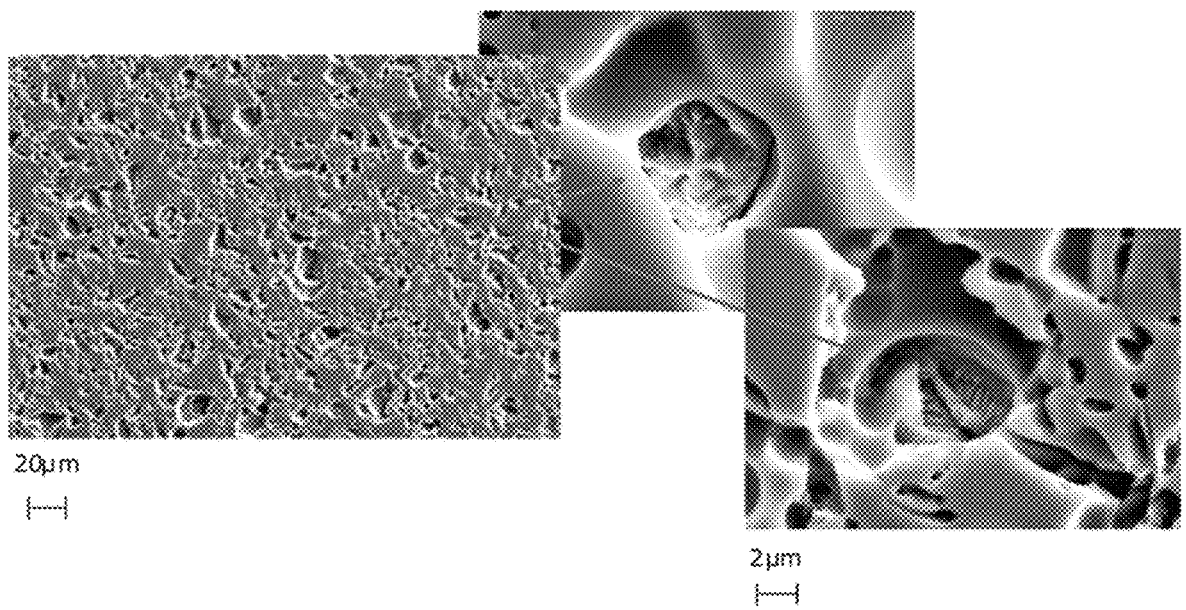

LOW-MELTING GLASS CERAMIC

CROSS REFERENCE TO RELATED APPLICATIONS

This application claims priority to and the benefit of European Patent Application No. 19172510.0 filed in the European Patent Office on May 3, 2019 and European Patent Application No. 20170631.4 filed in the European Patent Office on Apr. 21, 2020, the entire contents of which are incorporated herein by reference.

BRIEF DESCRIPTION OF THE DRAWINGS

A full and enabling disclosure of the present invention to one skilled in the art, including the best mode thereof, is set forth more particularly in the remainder of the specification, including reference to the accompanying figures, in which the Figure shows an SEM micrograph of a glass ceramic according to the one embodiment of the present invention.

The present invention relates to a glass ceramic for veneering a dental frame structure, wherein said glass ceramic is characterized by a high content of $B_2O_3$, to a process for the preparation thereof, and to the use thereof in the production of dental restorations.

Glass ceramics are materials that are prepared from glass melts by controlled crystallization. The glass is transferred into a partially polycrystalline and partially glassy ceramic state by specific temperature treatments to form a glass-like product whose properties are different from those of normal glasses, however.

Glass ceramics are employed in a variety of technical fields, one of the best known being as hobs and cookware in the household field. In addition to other applications, for example, as high performance reflectors for digital projectors, glass ceramics are also used as materials in the production of dental restorations.

Thus, for example, DE 197 50 794 describes lithium disilicate glass ceramic products that can be processed by plastic deformation under the action of pressure and heat or machining into shaped dental products having a high strength.

In addition to the production of the base body of the dental restoration, glass ceramics may also be employed as veneering materials, which are used to mimic the natural tooth based on a framework structure. In this application, the main thing that is important is a good bonding between the veneer and the framework structure in order to ensure a stable and durable dental restoration. A stable bonding is mostly achieved by matching the properties of the veneering material, especially in terms of thermal expansion, to those of the framework material.

WO 2018/071408 describes a dental restoration having a framework structure based on a lithium disilicate glass ceramic or a $ZrO_2$-based ceramic that contains at least one veneer coating, wherein said veneer coating is thermally compatible with said framework structure.

EP 2 405 883 discloses a composition to be used for attaching a dental facing on a dental support structure, the composition comprising from 10 to 55% by weight of water and from 40 to 85% by weight of a glass-ceramic material comprising from 55 to 75% by weight of silica and from 8 to 22% by weight of alumina. The veneer structure is proportionally enlarged by an enlargement factor of 1.12 to 1.9 as compared to a sintered veneer, and has a coefficient of thermal expansion of $8*10^{-6}$ $K^{-1}$ to $15.8*10^{-6}$ $K^{-1}$.

EP 1 000 588 relates to a ceramic dental restoration composed of a base ceramic based on a leucite-containing glass ceramic that is faced with a dental ceramic, wherein said base ceramic contains as components from 40 to 95% by weight $SiO_2$ and from 5 to 25% by weight $Al_2O_3$. The dental ceramic has a linear thermal expansion coefficient $\alpha_{(20-500° C.)}$ of $13.5*10^{-6}$ $K^{-1}$ to $17.0*10^{-6}$ $K^{-1}$, and the base ceramic has a linear thermal expansion coefficient $\alpha_{(20-500° C.)}$ of $12.5*10^{-6}$ $K^{-1}$ to $15.5*10^{-6}$ $K^{-1}$, in which the thermal expansion coefficient of the base ceramic is by $1.5*10^{-6}$ $K^{-1}$ lower than that of the veneer ceramic.

DE 102010035545 A1 discloses a veneer ceramic for dental restorations in which the framework ceramic is made of yttrium-stabilized zirconium dioxide. The veneer ceramic is based on lithium disilicate and is not to contain any leucite, lithium metasilicate or beta-spodumene. The veneer ceramics have a thermal expansion coefficient of more than $9.5*10^{-6}$ $K^{-1}$ according to the Examples.

U.S. Pat. No. 6,121,175 A discloses alkali silicate glasses and apatite glass ceramics that contain opacifiers, such as ZnO and $ZrO_2$. However, the compositions described have neither a sufficient temperature cycling resistance nor a suitable translucency or a suitable thermal expansion coefficient to be able to veneer both high temperature materials, such as zirconium dioxide, and lower melting ceramics, such as lithium disilicate and zirconia-stabilized lithium silicate ceramics.

EP 0 544 145 relates to a dental-ceramic material for producing and repairing cermet and fully ceramic dentures having a processing temperature of below 700° C. and a coefficient of thermal expansion $\alpha$ of $13-14*10^{-6}$ $K^{-1}$ at between 20 and 500° C., characterized by the composition: 60 to 65% by weight of $SiO_2$, 8.5 to 11% by weight of $Al_2O_3$, 8 to 12% by weight of $K_2O$, 10.5 to 12% by weight of $Na_2O$, 0.7 to 2% by weight of CaO, 0.6 to 2% by weight of BaO, 0.5 to 2.5% by weight of $B_2O_3$, 0.1 to 0.6% by weight of $Sb_2O_3$, 0 to 0.5% by weight of $CeO_2$, 1.2 to 3.8% by weight of $TiO_2$, 0.8 to 1.4% by weight of $Li_2O$, and 1.2 to 3.8% by weight of $F_2$.

In the production of dental restorations, the veneer structure is used to conceal the framework structure and to provide the restoration with as natural as possible an appearance, so that it is unobtrusively incorporated into the existing tooth scheme. Thus, the veneer structure is applied to the framework structure and, together with the latter, subjected to thermal treatment, which is to provide for a strong bonding between the framework and veneer structures on the one hand, and serves for adjusting the optical properties of the dental restoration on the other. Although the glass ceramics described in the prior art are matched to the common framework materials in their thermal behavior, it happens time and again in practice that cracks and fissures form in the veneer structure because of the different thermal expansion behaviors of the materials employed, whereby the dental restorations becomes useless.

Another drawback of the glass ceramics known in the prior art is their high softening point, which complicates processing and requires accordingly high temperatures in the production process, which considerably extends the time to completion of the dental restoration. In addition, another drawback of the mentioned high-melting veneering materials is the fact that their firing temperature exceeds the softening point of the glass ceramics used to form the framework structure, especially in cases where the framework structure consists of lithium silicate glass ceramics. The softening point of such glass ceramics is usually from 780 to 840° C., depending on the composition. The veneering of frameworks from this group of materials, which has become widespread in the meantime in the dental market, is not possible thereby, because the framework would become deformed during the firing of the veneering material. Problems with high-melting veneering materials are also found in $ZrO_2$ framework materials.

Although the softening point of $ZrO_2$ is far above the softening point of all known veneering materials, porously presintered $ZrO_2$ frameworks colored with coloring liquids are often employed in the dental branch in order to meet the patient's tooth color as well as possible. However, if these colored $ZrO_2$ frameworks are again heated at temperatures above 850° C. after the dense-sintering, coloring components contained therein are partially oxidized, and deviations in color fidelity will occur, depending on the composition of the coloring liquid employed.

Therefore, it is the object of the present invention to provide a glass ceramic for veneering a frame structure, which has a good processability and forms a stable bonding with the framework structure on the one hand. In addition, the glass ceramic is to be characterized by good optical properties which enable the natural color gradient of a tooth to be reproduced.

Surprisingly, it has been found that this object is achieved by a glass ceramic having a high content of $B_2O_3$.

Therefore, the present invention firstly relates to a glass ceramic for veneering a dental framework structure, containing $SiO_2$ in an amount of from 60 to 75% by weight, preferably from 65 to 70% by weight, and $B_2O_3$ in an amount of from 6 to 12% by weight, preferably from 7 to 10% by weight, and from 6 to 12% by weight of $K_2O$, respectively based on the total weight of the glass ceramic.

The glass ceramic according to the invention is characterized, in particular, by a comparably low softening point, which is why a material-saving processing is possible, which is important, in particular, with respect to the temperature sensitivity of the materials used for the framework structures. Surprisingly, it has been found that the deformation of the framework structure, which would usually occur otherwise, is reduced because of the low processing temperature of the glass ceramic associated with the its softening temperature, and the bonding between the veneer ceramic and the framework structure can be improved. Within the scope of the present invention, it has been found particularly advantageous if the softening point of the glass ceramic is not higher than 800° C. Therefore, an embodiment of the glass ceramic according to the invention is preferred in which the glass ceramic has a softening point of lower than 790° C., preferably lower than 780° C., more preferably from 730 to 770° C. The softening point can be determined by using heating microscopy, as set forth in DIN 51730, for example.

In particular, the properties of the glass ceramic according to the invention are matched to the properties of the materials used for producing the framework structure in order to ensure a stable bonding between the framework structure and the veneer ceramic. The glass ceramic may contain further components for adjusting its thermal properties, in particular.

In a preferred embodiment, the glass ceramic according to the invention further contains $K_2O$ in an amount of from 7 to 9% by weight, respectively based on the total weight of the glass ceramic. The presence of $K_2O$ in the compositions according to the invention favors the formation of leucite crystals in the glass ceramics according to the invention. The presence of leucite crystals in the glass ceramics according to the invention enhances the physical properties and the acid resistance. In a preferred embodiment of the present invention, the glass ceramics contain leucite ($K[AlSi_2O_6]$). In a further embodiment of the present invention, the glass ceramic has a crystal phase that preferably contains leucite as its main component.

In one embodiment, the glass ceramic contains leucite in an amount of from 0.1 to 10% by weight, preferably in an amount of from 0.2 to 5% by weight, or from 1 to 4% by weight. The leucite content can be determined by the Rietveld method.

In a further preferred embodiment, the glass ceramic contains $Al_2O_3$ in an amount of from 3 to 11% by weight, preferably from 5 to 9% by weight. $Al_2O_3$ also favors the obtaining of leucite crystals in the glass ceramics according to the invention.

The presence of $Na_2O$ also proved to be advantageous. Therefore, an embodiment is preferred in which the glass ceramic according to the invention contains $Na_2O$ in an amount of from 4 to 11% by weight, preferably from 5 to 7% by weight, respectively based on the total weight of the glass ceramic.

The interaction of $B_2O_3$ and $K_2O$ in the amounts to be employed according to the invention has proven particularly positive for the structural strengthening of the glass ceramic.

In contrast to other alkali oxides, the presence of $Li_2O$ in the glass ceramic has proven little advantageous, especially in view of the composite adhesion with the framework structure. Therefore, an embodiment of the glass ceramic according to the invention is preferred in which the content of $Li_2O$ in the glass ceramic is less than 3% by weight, preferably less than 2% by weight, more preferably from 0.1 to 1.5% by weight, respectively based on the total weight of the glass ceramic. In addition, the low content of $Li_2O$ results in the avoidance of the formation of lithium silicate crystals in the glass ceramics according to the invention.

Preferably, the presence of lithium silicate crystals in the glass crystals according to the invention is to be kept low in order not to adversely affect the physically and chemically advantageous properties.

In another advantageous embodiment of the present invention, the amount of lithium silicate crystals is less than 1% by weight, especially less than 0.1% by weight, and especially less than 0.01% by weight, based on the total weight of the glass ceramic. Particularly preferred is a glass ceramic that is essentially free of lithium disilicate and/or lithium metasilicate. "Essentially free" within the meaning of the present invention means a content below 0.01% by weight, but preferably totally free. The content of lithium silicate crystals in a glass ceramic can be determined by the Rietveld method.

In a particularly preferred embodiment, the glass ceramic according to the invention includes the following components:
  from 60 to 75% by weight, preferably from 65 to 70% by weight, of $SiO_2$;
  from 6 to 12% by weight, preferably from 7 to 10% by weight, of $B_2O_3$;
  from 6 to 12% by weight, preferably from 7 to 9% by weight, of $K_2O$;
  from 3 to 11% by weight, preferably from 5 to 9% by weight, of $Al_2O_3$;
  from 4 to 11% by weight, preferably from 5 to 7% by weight, of $Na_2O$;
  from 0 to 3% by weight, preferably from 0.1 to 1.5% by weight, of $Li_2O$;
  wherein the percentages by weight are respectively based on the total weight of the glass ceramic.

For improving the translucency, it has proven advantageous if the glass ceramics according to the invention contains the components selected from the group consisting of BeO, $TiO_2$, ZnO, BaO, $P_2O_5$, PbO, $CaF_2$ and NaF only in low amounts, preferably below 1.5% by weight, especially below 1.0% by weight, and specifically below 0.5% by weight, or below 0.1% by weight. Glass ceramics that are essentially free of the above mentioned components are also preferred.

In a further preferred embodiment, the glass ceramic according to the invention contains less than 0.5% by weight of ZnO, preferably less than 0.1% by weight of ZnO, respectively based on the total weight of the glass ceramic. An embodiment of the present invention in which the glass ceramic according to the invention is essentially free of ZnO is particularly preferred.

Further preferred is an embodiment in which the glass ceramic according to the invention contains less than 15% by weight of $ZrO_2$, preferably less than 5% by weight of $ZrO_2$, more preferably less than 1% by weight of $ZrO_2$, respectively based on the total weight of the glass ceramic. An embodiment of the present invention in which the glass ceramic according to the invention is essentially free of $ZrO_2$ is particularly preferred.

Further preferred is an embodiment in which the glass ceramic according to the invention contains less than 0.5% by weight of BaO, preferably less than 0.1% by weight of BaO, respectively based on the total weight of the glass ceramic. An embodiment of the present invention in which the glass ceramic according to the invention is essentially free of BaO is particularly preferred.

In another embodiment of the present invention, the total of the components consisting of BaO and ZnO is below 1.0% by weight, preferably below 0.5% by weight, and especially below 0.1% by weight, the weight percentages being respectively based on the total weight of the glass ceramics.

Those skilled in the art of glass ceramics are aware of the fact that the stating the components of the glass ceramic in the form of their oxides is a usual method for describing a glass ceramic. Nevertheless, it may be clarified here that the glass ceramic according to the invention is preferably obtained from a starting mixture containing the components of the glass ceramic in the form of their oxides.

In a preferred embodiment of the present invention, the glass ceramic according to the invention has a translucency above 75%, especially above 80%.

For determining the translucency, thin disks (1.5 g, diameter>14 mm) were compressed from ceramic powder and fired in a dental furnace for testing. Subsequently, the disks were brought to a final thickness of 1.00±0.01 mm by grinding and polished to a high gloss on both sides. The measurement was effected with a commercially available photospectrometer in the visible range of the light spectrum (360 to 740 nm).

The glass ceramic according to the invention is characterized by forming a stable bonding with the framework structure and thus avoiding chipping or damage under load, for example, during the chewing process, even for a low veneer thickness. This advantageous composite is achieved, in particular, because the coefficient of thermal expansion CTE of the glass ceramic is matched to that of the material of the framework structure. The CTE of the glass ceramic according to the invention must by no means exceed the CTE of the framework. It has proven particularly advantageous if the CTE of the glass ceramic according to the invention is by 0.1 to $2.5*10^{-6}K^{-1}$ below the CTE of the framework structure. Therefore, an embodiment is preferred in which the glass ceramic has a coefficient of thermal expansion, CTE, of less than $9.5*10^{-6}K^{-1}$, preferably of $9.3*10^{-6}K^{-1}$ or less, more preferably from $8.3*10^{-6}K^{-1}$ to $9.3*10^{-6}K^{-1}$, or from $8.3*10^{-6}K^{-1}$ to $9.0*10^{-6}K^{-1}$, as determined by using a dilatometer. The coefficient of thermal expansion was determined at a temperature below 800° C., especially within a range of from 100 to 400° C.

The glass ceramic according to the invention is further characterized by a high chemical stability, which makes it suitable especially for use in the dental field. Surprisingly, it has been found that the glass ceramic according to the invention has a low solubility, especially in acidic media, despite the high content of $B_2O_3$. Therefore, an embodiment is preferred in which the glass ceramic according to the invention has a solubility of less than 20 μg/cm², preferably less than 10 μg/cm², more preferably from 1 to 5 μg/cm². The solubility may be determined according to DIN ISO 6872, for example.

The glass ceramic is preferably provided in the form of a powder, which is processed into a paste by using a liquid medium, which paste is then applied to the framework structure. Surprisingly, it has been found that the composite adhesion between the glass ceramic and the framework structure can be increased if the glass ceramic is employed in the form of a powder having a selected particle size distribution. Therefore, an embodiment is preferred in which the glass ceramic is in the form of a powder having a particle size distribution D50 of from 15 to 35 μm, preferably from 20 to 25 μm, as determined by using a laser granulometer. Further preferably, the glass ceramic according to the invention in the form of a powder has a particle size distribution D90 of from 50 to 80 μm, preferably from 60 to 75 μm, as determined by using a laser granulometer. In a preferred embodiment, the glass ceramic according to the invention in the form of a powder has a particle size distribution D10 of from 2 to 10 μm, preferably from 3 to 5 μm, as determined by using a laser granulometer.

In particular, adjusting the particle size distribution of the glass ceramic according to the invention has proven an important factor in the formation of a stable bonding between the framework structure and the glass ceramic. The particle size distribution can be achieved, for example, by subjecting the glass ceramic to several milling and melting processes during the preparation thereof. Therefore, the present invention further relates to a process for preparing the glass ceramic according to the invention, comprising the following steps:

a) preparing a starting glass by melting the base components and quenching the melt in water;
b) milling the glass from step a) to obtain a powder;
c) pressing the powder from step b) to obtain a blank;
d) thermally treating the blank to obtain a glass ceramic; and
e) milling the blank from step d) to obtain a powder.

Preferably, the preparation of the glass in step a) of the process according to the invention is effected from a starting mixture containing the components of the glass ceramic in the form of their oxides.

In a preferred embodiment of the present invention, the production of the starting glass in step a) is performed in two stages. Thus, in a step a-i), a leucite partial frit powder capable of forming leucite crystals is prepared at first. The preparation of the leucite partial frit powder is preferably effected by melting the base components for the leucite partial frit, followed by quenching in water and optionally grinding the thus obtained leucite partial frit. Preferably, the leucite partial frit powder has the following composition:

from 50 to 60% by weight, preferably from 52 to 58% by weight, of $SiO_2$;

from 12 to 18% by weight, preferably from 13 to 17% by weight, of $K_2O$;

from 12 to 18% by weight, preferably from 13 to 17% by weight, of $Al_2O_3$;

optionally from 4 to 10% by weight, preferably from 5 to 9% by weight, of $Na_2O$;

optionally from 1.5 to 6% by weight, preferably from 2 to 5% by weight, of $B_2O_3$;

optionally from 0.5 to 3% by weight, preferably from 1.0 to 2.5% by weight, of CaO; and optionally from 0 to 2% by weight, preferably from 0.5 to 1.6% by weight, of $Li_2O$.

Further, in a step a-ii), a glass partial frit powder is prepared, which is amorphous. The preparation of the glass partial frit powder is preferably effected by melting the base components for the glass partial frit, followed by quenching in water and optionally grinding the thus obtained glass partial frit. The composition of the glass partial frit is selected to yield the composition of the glass ceramic according to the invention when mixed with the leucite partial frit from step a-i). Preferably, the glass partial frit powder has the following composition:

from 65 to 80% by weight, preferably from 68 to 75% by weight, of $SiO_2$;

from 4 to 10% by weight, preferably from 5 to 9% by weight, of $K_2O$;

from 2 to 10% by weight, preferably from 3 to 9% by weight, of $Al_2O_3$;

optionally from 4 to 10% by weight, preferably from 5 to 8% by weight, of $Na_2O$;

optionally from 5 to 12% by weight, preferably from 6.5 to 10% by weight, of $B_2O_3$;

optionally from 0.5 to 3% by weight, preferably from 1.0 to 2.5% by weight, of CaO; and optionally from 0 to 2% by weight, preferably from 0.5 to 1.6% by weight, of $Li_2O$.

The powders obtained from step a-i) and step a-ii) can subsequently be mixed at a suitable mixing ratio. The mixing ratio of leucite partial frit powder to the glass partial frit powder is selected to obtain the compositions of the glass ceramics according to the invention. Usually, the weight ratio of leucite partial frit powder to glass partial frit powder is from 1:20 to 1:1, preferably from 1:10 to 1:2.

The powder mixtures are subsequently further processed according to steps c) to e). The thermal treatment in step d) preferably results in the formation of leucite crystals.

The thermal treatment to form the glass ceramic in step d) of the process according to the invention is preferably performed at a temperature of 800 to 900° C., preferably 820 to 880° C., more preferably 830 to 850° C.

The glass ceramic according to the invention is suitable, in particular, for preparing veneer structures applied to framework structures to obtain a dental restoration. Therefore, the present invention further relates to the use of the glass ceramic according to the invention for veneering a framework structure, preferably a ceramic framework structure based on lithium disilicate or $ZrO_2$.

For achieving a stable bonding between the veneer structure and the framework structure, it has proven advantageous if the veneer structure and the framework structure have similar coefficients of thermal expansion. Therefore, an embodiment is preferred in which the difference between the coefficient of thermal expansion of the veneer structure, $CTE_{VS}$, and the coefficient of thermal expansion of the framework structure, $CTE_{FS}$, is not more than $2.5*10^{-6}$ $K^{-1}$, preferably less than $1.5*10^{-6}$ $K^{-1}$, more preferably less than $1.0*10^{-6}$ $K^{-1}$, wherein the framework structure has a higher CTE as compared to the veneer structure, and the coefficient of thermal expansion can be respectively determined by using a dilatometer.

The present invention further relates to a dental restoration including a framework structure and a veneer structure, wherein said veneer structure is a glass ceramic according to the present invention. The framework structure is preferably a ceramic framework structure based on lithium disilicate or $ZrO_2$. The framework structure can be designed to reproduce the natural color gradient of a tooth. In this way, the complicated coloring of the veneer structure is avoided. The coloring of the framework structure may be effected, for example, by introducing coloring oxides, or by using coloring solutions. Surprisingly, it has been found that the optical properties of the framework are not affected by firing the veneer structure.

Therefore, an embodiment is preferred in which the framework structure has a color gradient. Alternatively, an embodiment is preferred in which the framework structure is colored.

Surprisingly, it has been found that a stable bonding between the veneer structure and the framework structure can be achieved by means of the glass ceramic according to the invention, even for a low thickness of the veneer structure. Therefore, an embodiment is preferred in which the thickness of the veneer structure is from 0.2 to 3 mm, preferably from 0.5 to 1.5 mm.

For achieving such a low thickness, it has proven advantageous if the veneer structure is applied to the framework structure in the form of a paste. Therefore, the present invention further relates to a paste comprising a liquid medium and the glass ceramic according to the invention. Preferably, the liquid medium is water, which may optionally contain further components.

The present invention further relates to a process for preparing a dental restoration in which a glass ceramic according to the present invention or a paste according to the present invention is applied to a framework structure. In a preferred embodiment, the framework structure is a ceramic framework structure, especially based on lithium disilicate or $ZrO_2$.

The present invention is further explained by means of the following Examples, which are by no means to be understood as limiting the idea underlying the invention.

FIG. 1 shows an SEM micrograph of a glass ceramic according to the invention in accordance with Example Part II. The glass ceramic was treated with 5% HF for 90 seconds. The etched spots indicate the positions where leucite was present.

EXAMPLES

Example Part I

The glass ceramic according to the invention was applied as a veneering material to different framework structures, and the temperature cycling resistance according to DIN EN ISO 9693-2:2016-07 was tested. Thus, the veneered framework structures were alternately heated in the oven and then quenched in ice water, in which the oven temperature was increased by 15° C. after each quenching. The holding time in the oven was 30 minutes each, and the test specimens were examined for cracking and chipping after each quenching. The results are summarized in the following Tables.

The glass ceramics according to the invention had a content of $B_2O_3$ of 8% by weight. For comparison, conventional glass ceramics having a content of $B_2O_3$ of 1% by weight (Comparison 1) or 5% by weight (Comparison 2) were used.

TABLE 1

Temperature cycling resistance
(DIN EN ISO 9693-2:2016-07)
on lithium disilicate as
the framework material

|  | Glass ceramic according to the invention | Comp. 1 | Comp. 2 |
|---|---|---|---|
| fissures at 105° C. | none | none | none |
| fissures at 120° C. | none | none | none |
| fissures at 135° C. | none | none | yes |
| fissures at 150° C. | none | none | yes |
| fissures at 165° C. | none | yes | yes |
| undamaged specimens | 7/7 | 5/7 | 0/7 |

TABLE 2

Temperature cycling resistance on $ZrO_2$ frameworks

|  | Glass ceramic according to the invention | Comp. 1 | Comp. 2 |
|---|---|---|---|
| fissures at 105° C. | none | none | none |
| fissures at 120° C. | none | none | none |
| fissures at 135° C. | none | yes | yes |
| fissures at 150° C. | none | none | yes |
| fissures at 165° C. | yes | yes | — |
| undamaged specimens | 5/7 | 1/7 | 0/7 |

Further, the composite adhesion of the veneering materials with framework materials based on ZrO2 was determined using the detaching/initial cracking test (DIN EN ISO 9693-2:2016-07). The results are summarized in Table 3.

TABLE 3

|  | Mean value [M Pa] | Standard deviation [M Pa] |
|---|---|---|
| Glass ceramic according to the invention | 45.5 | 5.9 |
| Comp. 1 | 32.4 | 6.3 |
| Comp. 2 | 36.8 | 4.8 |

As can be seen from the Table, the glass ceramic according to the invention has an excellent composite bonding. The softening point of the glass ceramic according to the invention was determined by heating microscopy at 762° C.

Example Part II

The exemplary compositions MU/034/18, MU/035/18 and MU/036/18 are final frits that are respectively composed of 2 partial frits. One partial frit each is a leucite frit with a high CTE. After the thermal treatment, leucite crystals crystallize in the leucite frit. The other partial frit is respectively a glass frit with a low CTE. The glass frit remains amorphous even after the thermal treatment and does not form any crystals.

The glass frit and leucite frit are mixed at a ratio in which a certain fraction of the leucite will crystallize after the thermal treatment, by which the desired CTE of the final frit is in turn adjusted.

The preparation of the final frits is effected by mixing, melting and subsequently quenching in water the components of the glass frit and of the leucite frit, each independently of one another. The respectively quenched powders are ground to a powder. The thus obtained partial frit powders of the leucite frit and the glass frit are subsequently mixed together in the weight percentages as stated in Table 4. Subsequently, the powder mixture is compressed to a blank, and the blank is subjected to thermal treatment to obtain the glass ceramic. During the thermal treatment, leucite crystals are formed. The thermally treated blank is subsequently ground to obtain the final frit powder.

The following 3 final frits and 4 partial frits are described in the following, and are listed in the Table below:

TABLE 4

|  | Partial frits | |
|---|---|---|
| Final frits | Leucite frit (and its weight percentage) | glass frit (and its weight percentage) |
| MU/034/18 | SD (22.5%) | HAK109 (77.5%) |
| MU/035/18 | HAK105 (10%) | HAK108 (90%) |
| MU/036/18 | HAK105 (22.5%) | HAK109 (77.5%) |

Chemical Composition:

The chemical composition of all Examples was determined. The determination of the contents of the following oxides was performed using X-ray fluorescence: $SiO_2$, MgO, $Na_2O$, $Fe_2O_3$, MnO, $TiO_2$, $P_2O_5$, CaO, $K_2O$, $Al_2O_3$, BaO, ZnO, $ZrO_2$, $SnO_2$, $Cr_2O_3$, CoO, NiO, $Sb_2O_3$, $La_2O_3$, $CeO_2$. The contents of the following oxides were determined by atomic absorption spectrometry after KOH digestion: $B_2O_3$, $Li_2O$.

The ignition loss was determined according to DIN EN ISO 26845:2008-06 Section 9 (1050±50° C./1 h). In Table 5 as shown below, only those components that were 0.01% by weight according to the analytical result were considered.

Since the chemical compositions of all partial frits are available, it is possible to calculate the chemical composition of the final frits from those of the partial frits (Table 6).

Material Properties:

For determining the combustion temperature, thin disks (0.7 g) were compressed from ceramic powder and fired in a dental furnace for testing.

The following material properties were determined according to ISO 6872: Coefficient of thermal expansion (CTE), acid solubility and bending strength. According to ISO 6872, the glass ceramic according to the invention is classified as Type I ceramic and as class 1b. The test instructions and minimum specification for this type or this class apply accordingly. Since Type I ceramics can be influenced by the repeated firing, the CTE is determined after two and four firings of the specimen according to the standard, wherein as low as possible a difference between the two measuring results was to be achieved.

The following material properties were determined according to ISO 9693: temperature cycling resistance and debonding/crack initiation test. The temperature cycling resistance is possible for all framework materials that match to the ceramic according to the invention in terms of CTE. The debonding/crack initiation test is approved only for zirconia frameworks.

TABLE 5

Chemical compositions according to analytical result

| | Partial frits | | | | End frits | |
| --- | --- | --- | --- | --- | --- | --- |
| | Leucite frits | | Glass frits | | | |
| wt. % | SD | HAK105 | HAK108 | HAK109 | MU/034/18 | MU/036/18 |
| $SiO_2$ | 54.41 | 55.98 | 70.70 | 71.62 | 66.21 | 67.46 |
| $K_2O$ | 14.23 | 16.04 | 7.69 | 6.13 | 8.16 | 8.30 |
| $Al_2O_3$ | 15.51 | 14.03 | 8.85 | 4.24 | 7.21 | 6.32 |
| $Na_2O$ | 8.68 | 6.16 | 6.45 | 5.65 | 6.29 | 5.50 |
| $B_2O_3$ | 4.76 | 3.12 | 2.59 | 8.34 | 8.31 | 7.84 |
| CaO | 1.28 | 1.98 | 1.34 | 2.13 | 1.92 | 2.10 |
| $Li_2O$ | <0.01 | 1.46 | 1.68 | 0.90 | 0.78 | 1.15 |
| $TiO_2$ | 0.37 | 0.01 | 0.04 | 0.02 | 0.11 | 0.01 |
| $P_2O_5$ | 0.02 | <0.01 | <0.01 | <0.01 | 0.02 | <0.01 |
| $Fe_2O_3$ | <0.01 | 0.03 | 0.02 | 0.02 | 0.03 | 0.02 |
| MgO | <0.01 | 0.02 | 0.02 | 0.04 | 0.02 | 0.03 |
| $ZrO_2$ | <0.01 | 0.01 | 0.02 | 0.03 | <0.01 | 0.02 |
| BaO | 0.01 | 0.08 | <0.01 | <0.01 | 0.06 | 0.02 |
| Ignition loss | 0.30 | 0.27 | 0.29 | 0.07 | 0.11 | 0.14 |
| Total | 99.57 | 99.19 | 99.68 | 99.19 | 99.23 | 98.91 |

TABLE 6

Chemical compositions according to the calculation from the analytical results of the partial frits:

| | Final frits | | |
| --- | --- | --- | --- |
| wt.% | MU/034/18 | MU/035/18 (Comp.) | MU/036/18 |
| $SiO_2$ | 66.89 | 69.23 | 68.10 |
| $K_2O$ | 8.36 | 8.53 | 8.36 |
| $Al_2O_3$ | 7.34 | 9.37 | 6.44 |
| $Na_2O$ | 6.48 | 6.42 | 5.76 |
| $B_2O_3$ | 7.35 | 2.64 | 7.17 |
| CaO | 1.90 | 1.40 | 2.10 |
| $Li_2O$ | 0.65 | 1.66 | 1.03 |
| $TiO_2$ | 0.12 | 0.04 | 0.02 |
| $P_2O_5$ | 0.01 | 0.00 | 0.00 |
| $Fe_2O_3$ | 0.01 | 0.02 | 0.02 |
| MgO | 0.03 | 0.02 | 0.04 |
| $ZrO_2$ | 0.02 | 0.02 | 0.03 |
| BaO | 0.00 | 0.01 | 0.02 |
| Ignition loss | 0.13 | 0.29 | 0.12 |
| Total | 99.29 | 99.65 | 99.21 |

TABLE 7

Material properties of the partial and final frits:

| Frit | Frit type | Firing temperature [° C.] | CTE (25-400° C.) [$10^{-6}$ $K^{-1}$] 2× fired | CTE (25-400° C.) [$10^{-6}$ $K^{-1}$] 4× fired | Acid solubility [μg/cm$^2$] | Bending strength Mpa |
| --- | --- | --- | --- | --- | --- | --- |
| SD | Leucite frit | 750 | 18.3 | 19.5 | — | — |
| HAK105 | Leucite frit | 820 | 18.4 | 18.1 | — | — |
| HAK108 | Glass frit | 760 | 8.5 | 8.7 | 5 | — |
| HAK109 | Glass frit | 770 | 7.3 | 7.2 | 4 | — |
| MU/034/18 | Final frit | 765 | 8.9 | 8.9 | 9 | 112 ± 29 |
| MU/035/18 (Comp.) | Final frit | 745 | 9.2 | 9.7 | 1 | 101 ± 13 |
| MU/036/18 | Final frit | 760 | 8.6 | 8.7 | 8 | 93 ± 16 |

TABLE 8

Composite strength of the final frits towards lithium
disilicate and zirconia frameworks:

Temperature cycling resistance on $ZrO_2$ frameworks

|  | MU/034/18 | MU/035/18 (Comp.) | MU/036/18 |
|---|---|---|---|
| fissures at 105° C. | none | none | none |
| fissures at 120° C. | none | none | none |
| fissures at 135° C. | none | yes | none |
| fissures at 150° C. | none | yes | yes |
| fissures at 165° C. | yes | none | yes |
| undamaged specimens | 5/7 | 1/7 | 4/7 |

Temperature cycling resistance on lithium disilicate frameworks

|  | MU/034/18 | MU/036/18 |
|---|---|---|
| fissures at 105° C. | none | none |
| fissures at 120° C. | none | none |
| fissures at 135° C. | none | none |
| fissures at 150° C. | none | none |
| fissures at 165° C. | none | none |
| undamaged specimens | 7/7 | 7/7 |

Debonding/crack initiation test on
commercially available $ZrO_2$ frameworks

| Veneer ceramic | Framework material | Mean value [MPa] | Standard deviation [MPa] |
|---|---|---|---|
| MU/034/18 | VITA YZ$^{(R)}$ T | 44.9 | 4.2 |
| MU/034/18 | VITA YZ$^{(R)}$ XT | 50.8 | 7.8 |
| MU/036/18 | VITA YZ$^{(R)}$ T | 45.5 | 5.9 |
| MU/036/18 | VITA YZ$^{(R)}$ XT | 28.3 | 3.2 |

The framework materials can be purchased from the company Vita Zahnfabrik, Germany.

Result:

The glass ceramics MU/034/18 and MU/036/18 according to the invention meet all the desired requirements: sufficiently low firing temperature, stable CTE after repeated firing at $9\pm0.5\times10^{-6}$ $K^{-1}$, high bending strength, low acid solubility.

The Comparative Example MU/035/18 is not CTE-stable after repeated firing. The CTE values after two and four firings deviate from each other by 0.5, which is too much (a maximum of 0.3 would be tolerable for the final frit). Further, the Comparative Example shows a poor temperature cycling resistance. In this case too, the specimen is fired four times to prepare the veneered frameworks.

The invention claimed is:

1. A glass ceramic for veneering a dental framework structure, characterized in that said glass ceramic contains
   from 60 to 75% by weight of $SiO_2$,
   from 6 to 12% by weight of $B_2O_3$,
   from 6 to 12% by weight of $K_2O$, and
   less than 0.5% by weight of ZnO
   respectively based on the total weight of the glass ceramic.

2. The glass ceramic according to claim 1, characterized in that said glass ceramic has a softening point of lower than 790° C., as determined according to a heating microscope.

3. The glass ceramic according to claim 1, characterized in that said glass ceramic contains $K_2O$ in an amount of from 7 to 9% by weight, based on the total weight of the glass ceramic.

4. The glass ceramic according to claim 1, characterized in that said glass ceramic further contains $Al_2O_3$ in an amount of from 3 to 11% by weight, based on the total weight of the glass ceramic.

5. The glass ceramic according to claim 1, characterized in that said glass ceramic further contains $Na_2O$ in an amount of from 4 to 11% by weight, based on the total weight of the glass ceramic.

6. The glass ceramic according to claim 1, characterized in that said glass ceramic further contains $Li_2O$ in an amount of less than 3% by weight, based on the total weight of the glass ceramic.

7. The glass ceramic according to claim 1, characterized in that said glass ceramic has a coefficient of thermal expansion, CTE, of less than $9.5*10^{-6}K^{-1}$, as determined by using a dilatometer.

8. The glass ceramic according to claim 1, characterized in that said glass ceramic has a solubility of less than 20 $\mu g/cm^2$, as determined according to DIN ISO 6872.

9. The glass ceramic according to claim 1, characterized in that said glass ceramic has a translucency above 75%.

10. The glass ceramic according to claim 1, characterized in that said glass ceramic is essentially free of lithium disilicate and/or lithium metasilicate.

11. The glass ceramic according to claim 1, characterized in that said glass ceramic includes leucite.

12. The glass ceramic according to claim 1, characterized in that said glass ceramic includes leucite in an amount of from 0.1 to 10% by weight.

13. A process for preparing a glass ceramic according to claim 1, characterized in that said process comprises the following steps:
   a) preparing a starting glass by melting base components and quenching the melt in water;
   b) milling the glass from step a) to obtain a powder;
   c) pressing the powder from step b) to obtain a blank;
   d) thermally treating the blank to obtain a glass ceramic; and
   e) milling the blank from step d) to obtain a powder.

14. A process for veneering a dental framework structure, the process comprising applying the glass ceramic according to claim 1 to form a veneer structure to the dental framework structure, wherein the dental framework structure comprises a ceramic framework structure based on lithium disilicate or $ZrO_2$.

15. The process according to claim 14, characterized in that the difference between the coefficient of thermal expansion of the veneer structure, CTEvs, and the coefficient of thermal expansion of the framework structure, CTEvs, is not more than $2.5^1 10^{-6}$ $K^{-1}$, wherein the coefficient of thermal expansion can be respectively determined by dilatometry.

16. A dental restoration including a framework structure and a veneer structure, characterized in that said veneer structure is a glass ceramic according to claim 1.

17. The dental restoration according to claim 16, characterized in that the thickness of the veneer structure is from 0.2 to 3 mm.

18. A paste comprising a liquid medium and a glass ceramic powder according to claim 1 in the form of a powder for veneering a dental framework structure.

19. A process for preparing a dental restoration, wherein the glass ceramic according to claim 1 is applied to a framework structure.

20. A process for preparing a dental restoration, wherein the paste of according to claim 18 is applied to a framework structure.

* * * * *